(12) United States Patent
Enomoto

(10) Patent No.: US 11,553,885 B2
(45) Date of Patent: Jan. 17, 2023

(54) PATIENT MONITOR WITH USER INPUT TO REARRANGE PATIENT DISPLAY AREAS

(71) Applicant: NIHON KOHDEN CORPORATION, Tokyo (JP)

(72) Inventor: Yoshinori Enomoto, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 229 days.

(21) Appl. No.: 16/896,838

(22) Filed: Jun. 9, 2020

(65) Prior Publication Data

US 2020/0397386 A1 Dec. 24, 2020

(30) Foreign Application Priority Data

Jun. 20, 2019 (JP) .............................. JP2019-114611

(51) Int. Cl.
| | |
|---|---|
| *G06F 3/0488* | (2022.01) |
| *G06F 3/0486* | (2013.01) |
| *G16H 40/20* | (2018.01) |
| *A61B 5/00* | (2006.01) |

(52) U.S. Cl.
CPC .......... *A61B 5/7435* (2013.01); *G06F 3/0486* (2013.01); *G06F 3/0488* (2013.01); *G16H 40/20* (2018.01)

(58) Field of Classification Search
CPC ... A61B 5/7435; G06F 3/0486; G06F 3/0488; G16H 40/20
See application file for complete search history.

(56) References Cited

U.S. PATENT DOCUMENTS

| | | | | |
|---|---|---|---|---|
| 9,665,264 | B1* | 5/2017 | Janiak | G06F 3/04812 |
| 2003/0009244 | A1* | 1/2003 | Engleson | G16H 40/40 |
| | | | | 700/86 |
| 2006/0247948 | A1* | 11/2006 | Ellis | G16H 40/20 |
| | | | | 715/764 |
| 2011/0074585 | A1* | 3/2011 | Harmon | G06Q 10/087 |
| | | | | 715/738 |
| 2011/0148622 | A1* | 6/2011 | Judy | G16H 40/67 |
| | | | | 340/539.12 |
| 2012/0078647 | A1* | 3/2012 | Grassle | G16H 15/00 |
| | | | | 715/810 |
| 2013/0044111 | A1* | 2/2013 | VanGilder | G01D 7/04 |
| | | | | 345/440 |

(Continued)

FOREIGN PATENT DOCUMENTS

JP 2017-113412 A 6/2017

*Primary Examiner* — Daniel Samwel
(74) *Attorney, Agent, or Firm* — Sughrue Mion, PLLC

(57) ABSTRACT

A patient monitor includes an acquiring section that acquires physiological information of a plurality of patients, a displaying section, a screen controller and an inputting section. The inputting section through which instructions for moving a display area for a patient are input. In accordance with instructions input through the inputting section, the screen controller executes one of processes of: interchanging a display area for a specific patient with a display area for another patient, and displaying a resulting image on the screen; deleting a display area for a specific patient from the screen; a process of moving a display area for a specific patient, and displaying a resulting image on the screen; and inserting a display area for a specific patient, and displaying a resulting image on the screen.

18 Claims, 15 Drawing Sheets

(56) References Cited

U.S. PATENT DOCUMENTS

| | | | |
|---|---|---|---|
| 2013/0145360 A1* | 6/2013 | Ricci | G06F 16/29 |
| | | | 717/174 |
| 2013/0268283 A1* | 10/2013 | Vann | G06Q 10/0633 |
| | | | 705/2 |
| 2013/0332871 A1* | 12/2013 | Bucur | G06F 3/0482 |
| | | | 715/834 |
| 2014/0266794 A1* | 9/2014 | Brown | A61B 5/0002 |
| | | | 600/509 |
| 2016/0139761 A1* | 5/2016 | Grosz | G06T 11/60 |
| | | | 715/769 |

* cited by examiner

| MENU | REC. | | | | |
|---|---|---|---|---|---|
| BED001 ch1059 JIRO K. 80 | BED007 ch1053 ICHIRO K. 85 |
| BED002 ch 1023 DISCHARGED | BED008 GORO K. 80 |
| BED003 ch1049 TARO K. 84 | BED009 ch 1041 DISCHARGED |
| BED004 ch1054 HARUKO K. 80 | BED010 ch1034 AKIKO K. 86 |
| BED005 SHIRO K. 81 | BED011 ch 1003 DISCHARGED |
| BED006 ch1031 80 | BED012 ch 1013 DISCHARGED |

| 160 | 170 |
|---|---|
| 1 | 7 |
| 2 DISCHARGED | 8 |
| 3 | 9 DISCHARGED |
| 4 | 10 |
| 5 | 11 DISCHARGED |
| 6 | 12 DISCHARGED |

| 160 | 170 |
|---|---|
| 1 | 7 |
| 2 DISCHARGED | 8 |
| 3 | 9 DISCHARGED |
| 4 | 10 |
| 5 | 11 DISCHARGED |
| 6 | 12 DISCHARGED |

| 160 | 170 |
|---|---|
| 1 | 7 |
| 2 DISCHARGED | 8 |
| 5 | 9 DISCHARGED |
| 4 | 10 |
| 3 | 11 DISCHARGED |
| 6 | 12 DISCHARGED |

115
113

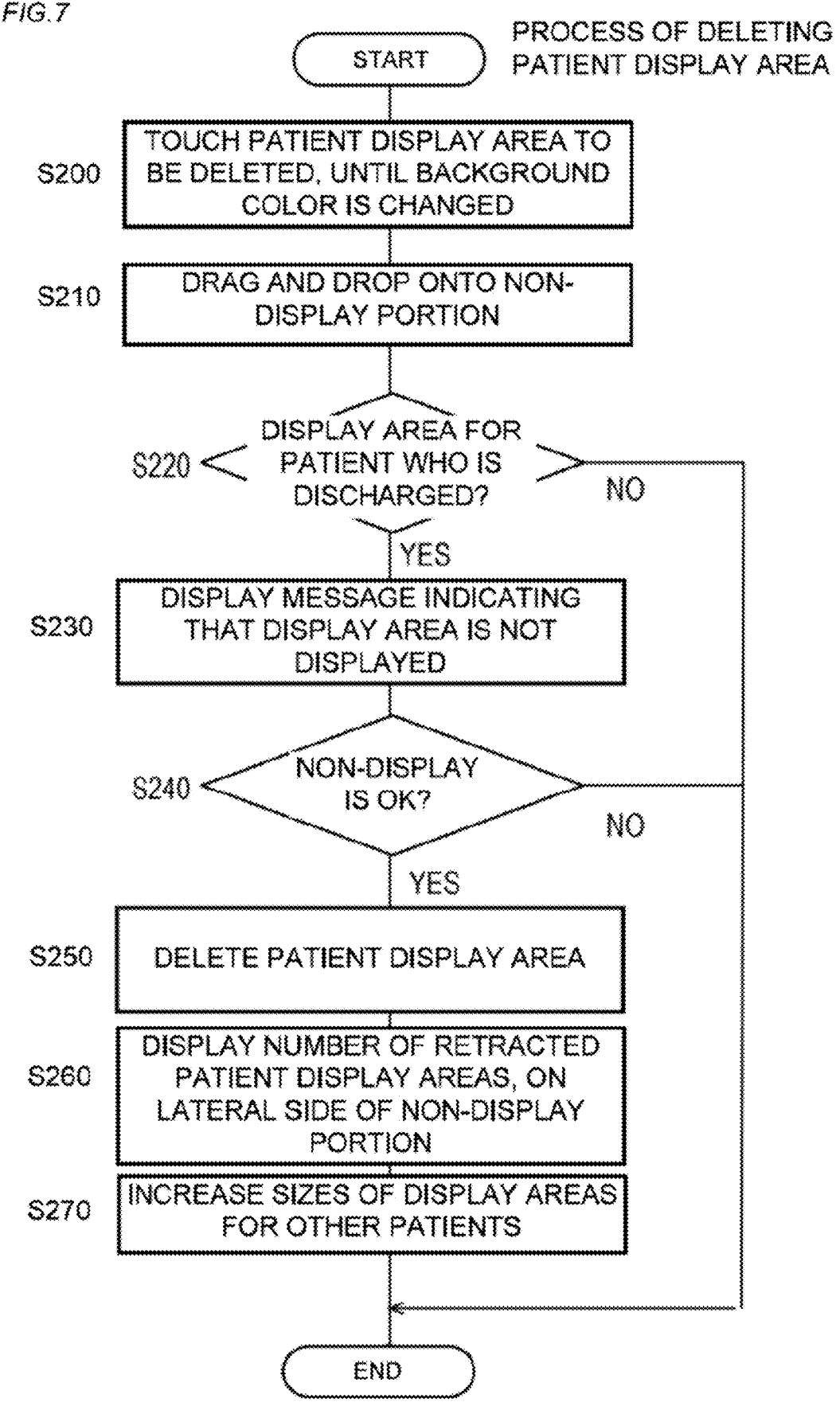

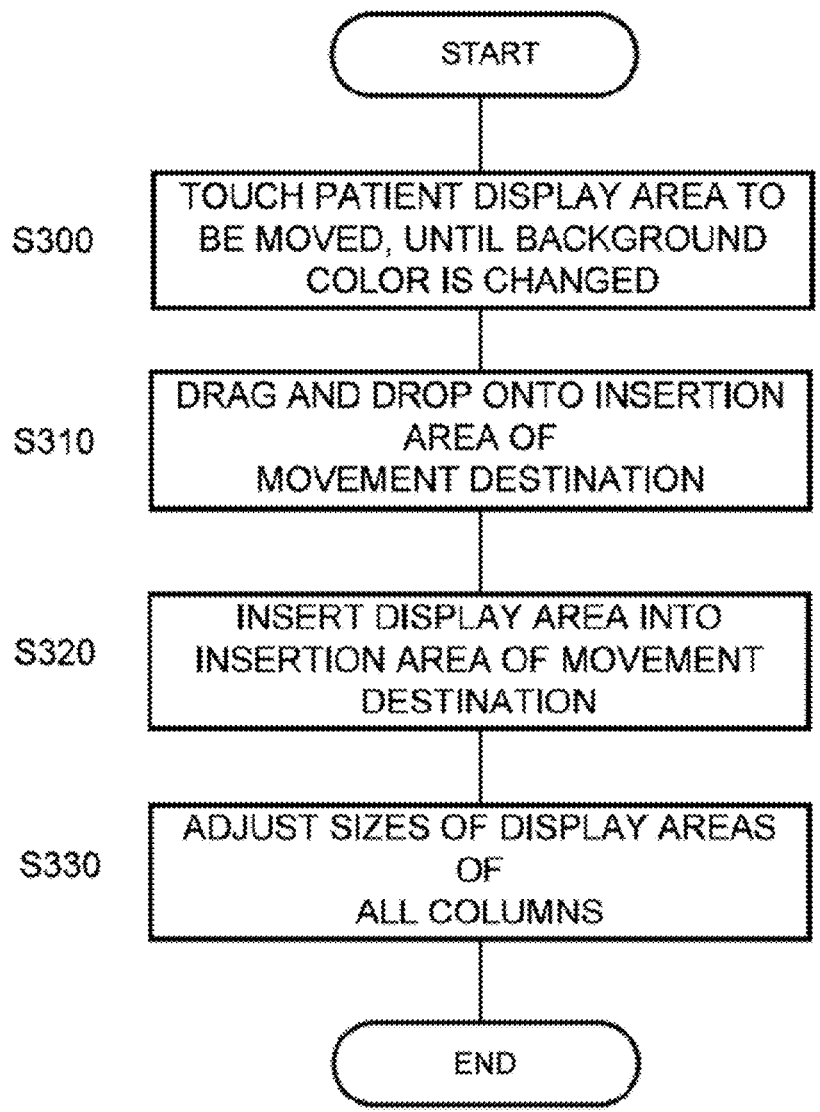

PATIENT MONITOR WITH USER INPUT TO REARRANGE PATIENT DISPLAY AREAS

CROSS-REFERENCE TO RELATED APPLICATIONS

The present application claims priority from Japanese Patent Application No. 2019-114611, filed Jun. 20, 2019, the entire content of which is incorporated herein by reference.

TECHNICAL FIELD

The presently disclosed subject matter relates to a patient monitor in which interchange, deletion, movement, and insertion of display areas for patients can be easily performed (hereinafter, a display area for a patient is sometimes referred to as "patient display area").

BACKGROUND ART

Usually, a central monitor is disposed in a nurse station. A central monitor collectively displays physiological information of a plurality of patients. Physiological information of patients is acquired from transmitters such as bedside monitors, telemeters, or the like that are disposed for the patients, respectively, in an intensive cure unit or a medical ward. Physiological information is vital data including electrocardiogram data, blood pressure data, arterial oxygen saturation ($SPO_2$) data, and the like.

A central monitor displays collected physiological information in display areas that are formed by dividing a screen, for each of patients. When the sizes or positions of the display areas are fixed for respective patients, however, the degree of freedom of arrangement by which the physiological information is made easily viewable is low. JP2017-113412 discloses a patient monitor in which a display area for a patient who is not in bed (discharged), and who is not required to be monitored is deleted by a plurality of touch operations that are performed by the user, and the display size of a display area for another patient who must be monitored is increased (Column Nos. 0046 to 0049, FIGS. 4 to 7).

SUMMARY

Even when the technique of the patient monitor disclosed in JP2017-113412 is used, however, interchange, deletion, movement, and insertion of patient display areas cannot be performed by a simple operation of the user.

Therefore, it is an object of the presently disclosed subject matter to provide a patient monitor in which interchange, deletion, movement, and insertion of patient display areas can be easily performed.

In order to attain the object, the patient monitor of the presently disclosed subject matter has an acquiring section, a displaying section, and a screen controller. The acquiring section acquires physiological information of a plurality of patients. The displaying section displays the physiological information of the plurality of patients that is acquired by the acquiring section, on a screen. The screen controller sets a plurality of display areas in the screen of the displaying section, and, in each of the set display areas, controls a display of the physiological information of patients that is acquired by the acquiring section.

The patient monitor further has an inputting section through which instructions for moving the display areas for each of patients are input. In accordance with instructions input through the inputting section, the screen controller executes one of processes of: interchanging a display area for a specific patient with a display area for another patient, and displaying a resulting image on the screen; deleting a display area for a specific patient from the screen; moving a display area for a specific patient, and displaying a resulting image on the screen; and inserting a display area for a specific patient, and displaying a resulting image on the screen.

According to the patient monitor of the presently disclosed subject matter, interchange, deletion, movement, and insertion of a plurality of patient display areas that are displayed on the screen can be easily performed.

According to the configuration, the position and size of a display area for a specific patient can be conveniently changed, or an unwanted patient display area can be deleted, with a result that the degree of freedom of arrangement of display areas is increased, and the physiological information of the specific patient can be easily known. Therefore, safer patient management is enabled.

BRIEF DESCRIPTION OF DRAWINGS

FIG. 1 is an external view of a patient monitor of an embodiment.

FIG. 5A illustrates a touch operation in the case where a patient display area is moved to a display area of the same column.

FIG. 5B illustrates a drag-and-drop operation in the case where a patient display area is moved to a display area of the same column.

FIG. 5C illustrates a screen in a state where a patient display area is interchanged with a display area of the same column.

FIG. 7 is an operational flowchart of a process of deleting a patient display area.

FIG. 11 is an operational flowchart of a process of moving a patient display area.

DETAILED DESCRIPTION

Hereinafter, an embodiment of the patient monitor of the presently disclosed subject matter will be described in detail with reference to the drawings.

Configuration of Patient Monitor

FIG. 1 is an external view of a patient monitor of the embodiment.

As illustrated in FIG. 1, the patient monitor 100 may include a display 110 that functions as the displaying section, and the body section 150. The patient monitor 100 may be, for example, a central monitor that is a dedicated apparatus to be disposed in a nurse station, or configured by using a commercially available personal computer.

A touch-panel type liquid crystal display or a touch-panel type organic EL display is used as the display 110. Although a touch-panel type liquid crystal display or a touch-panel type organic EL display is preferably used as the display 110, a display of another kind may be used.

On the display 110, as illustrated in be figure, sets of physiological information of twelve patients are displayed in display areas that are formed by dividing a screen, respectively. In the embodiment, the display areas for twelve patients are arranged in 6 rows and 2 columns on the screen of the display 110. The display areas are assigned to individual patients, respectively. In each of the display areas, physiological information of the patient assigned to the display area is displayed. In the display areas where "DISCHARGED" is displayed, physiological information of a patient is not displayed. The display areas contain information by which admit/discharge of a patient can be distinguished.

In the patient monitor 100, when the operator simply touches the screen with the finger, and drags and drops the touched patient display area onto another place, interchange, deletion, movement, or insertion of the touched patient display area can be easily performed. Although, in the embodiment, a drag-and-drop operation is performed by using the finger, a drag-and-drop operation may be performed by a left-click of a mouse or a touch pad.

Figure 2:
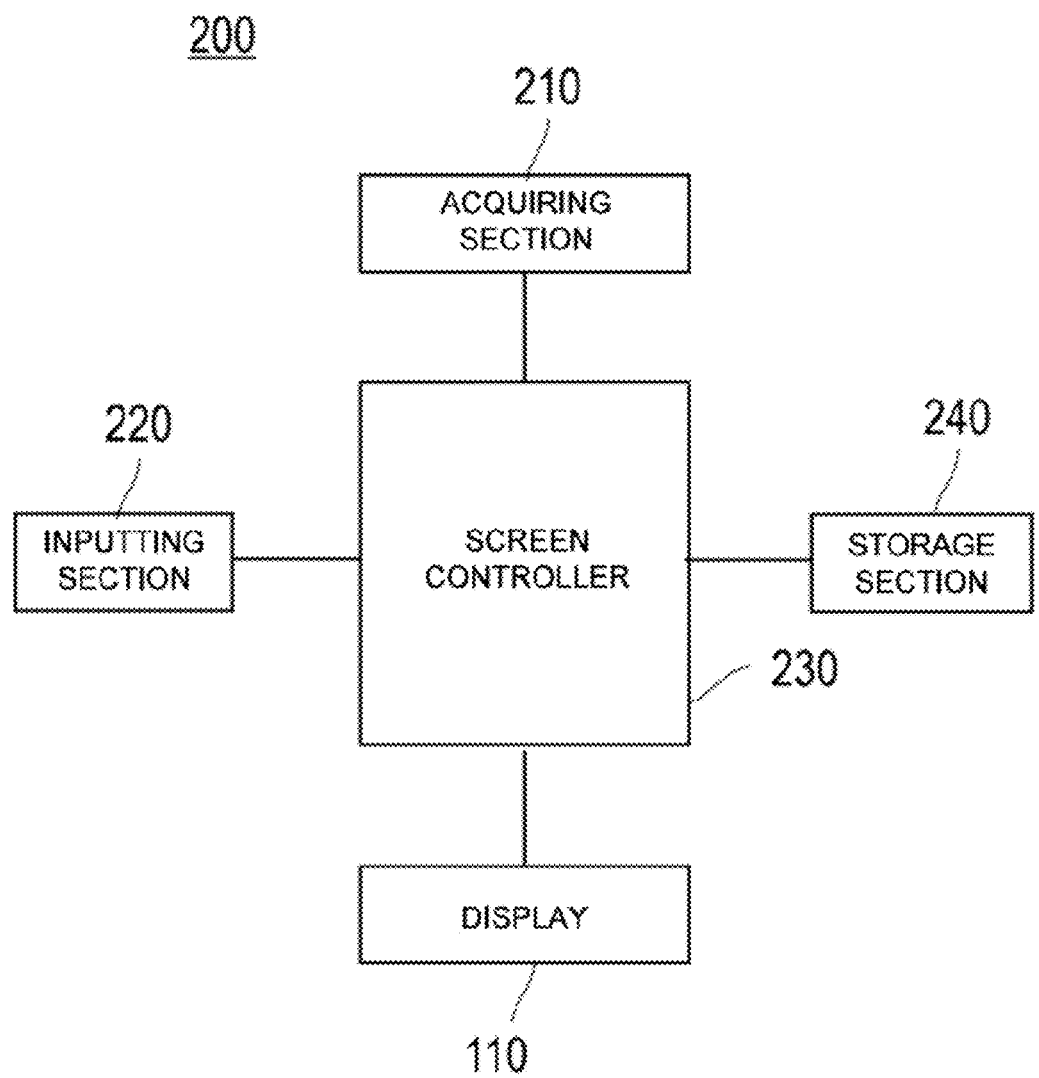
FIG. 2 is a block diagram of a control system of the patient monitor of the embodiment.

FIG. 2 is a block diagram of a control system of the patient monitor 100 of the embodiment. As illustrated in the figure, the control system 200 of the patient monitor 100 may include the display 110, an acquiring section 210, an inputting section 220, a screen controller 230, and a storage section 240.

The acquiring section 210 acquires physiological information of a plurality of patterns. Physiological information of patients is acquired, for example, from bedside monitors (not shown) that are disposed respectively for the patients in an intensive care unit or a medical ward. For example, physiological information of a patient is vital data including electrocardiogram data, invasive blood pressure data, non-invasive blood pressure data (NIBP), arterial oxygen saturation ($SPO_2$) data, respiration (RESP) data, and the like.

The inputting section 220 receives instructions for moving patient display areas. The inputting section 220 is a pointing device which includes a mouse, a touch pad, or a touch panel, and through which instructions for moving patient display areas can be given by a drag-and-drop operation. In the embodiment, since a touch-panel type liquid crystal display or a touch-panel type organic EL display is used as the display 110, the inputting section 220 is a touch panel that is disposed on the screen. When a touch panel, a mouse, a touch pad, or a pointing device including a touch panel is used, interchange, deletion, movement, and insertion of patient display areas can be easily performed.

The screen controller 230 sets a plurality of display areas in the screen of the display 110 as illustrated in FIG. 1, and causes the physiological information of the patients that are acquired by the acquiring section 210, to be displayed in the set display areas, respectively. In accordance with instructions input through the inputting section 220, the screen controller 230 further executes one of processes of: interchanging a display area for a specific patient illustrated in FIG. 1 with that of another patient, and displaying a resulting image on the screen; deleting a display area for a specific patient from the screen; moving a display area for a specific patient, and displaying a resulting image on the screen; and inserting a display area for a specific patient, and displaying a resulting image on the screen.

The storage section 240 stores programs for causing the screen controller 230 to execute the processes of: displaying physiological information of patients; interchanging a display area for a specific patient with that of another patient, and displaying a resulting image on the screen; deleting a display area for a specific patient from the screen; moving a display area for a specific patient, and displaying a resulting image on the screen; and inserting a display area for a specific patient, and displaying a resulting image on the screen.

Figure 3:
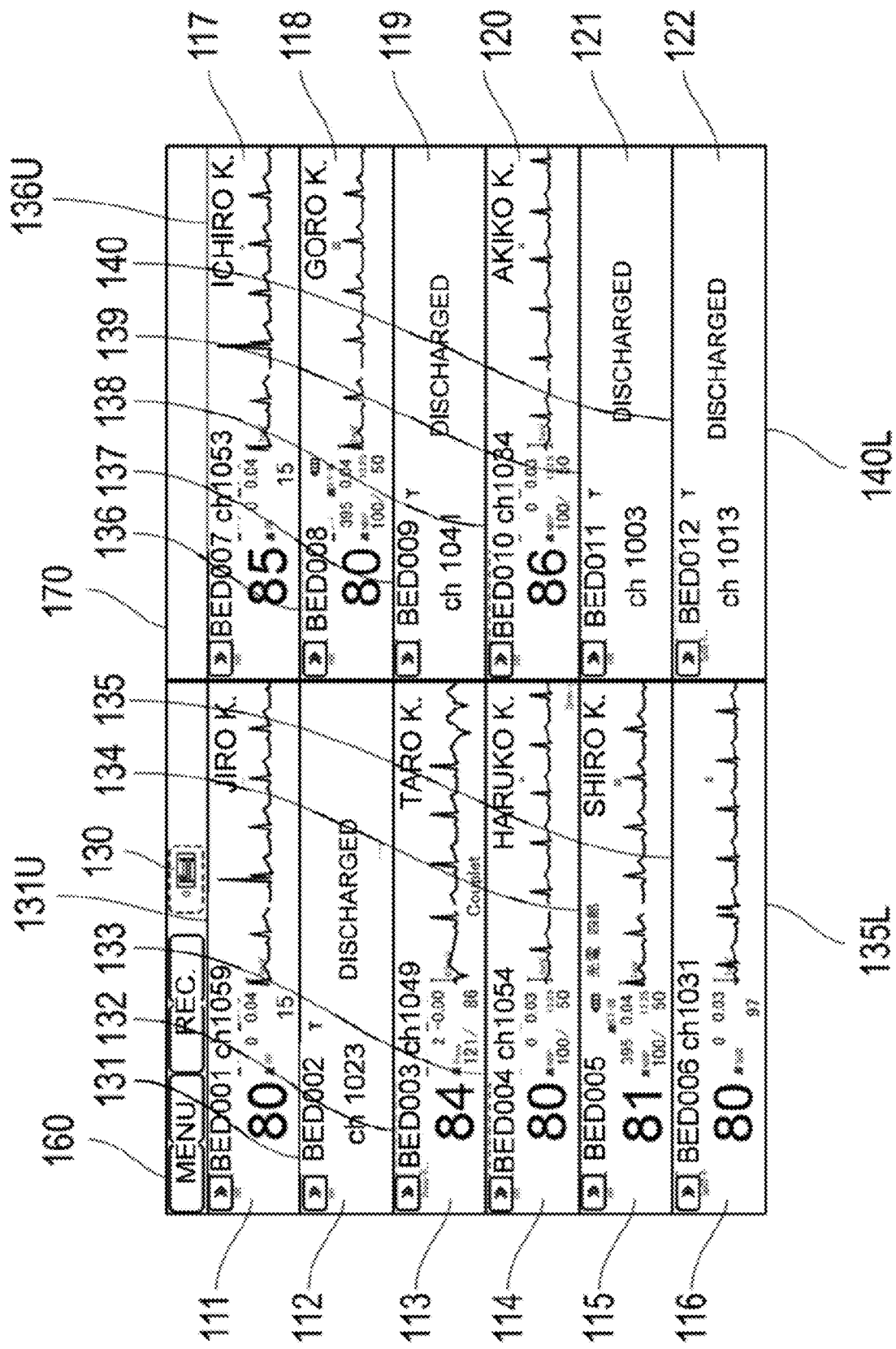
FIG. 3 is a view illustrating patient display areas, non-display portion, and insertion areas that are displayed on a display of the patient monitor of FIG. 1.

FIG. 3 is a view illustrating patient display areas, non-display portion, and insertion areas that are displayed on the display 110 of the patient monitor 100 of FIG. 1.

In the embodiment, the patient display areas are arranged in 6 rows and 2 columns. The arrangement in 6 rows and 2 columns is a mere example, and any kind of arrangement may be employed as far as the patient display areas are arranged in plural rows and plural columns. Patient display areas 111 to 116 are arranged in the first column 160, and patient display areas 117 to 122 are arranged in the second column 170.

Physiological information of Patient 1 is displayed in the patient display area 111, and that of Patient 2 is displayed in the patient display area 112. In the patient display areas 111 and 112, real time physiological information of patients is displayed, and it is indicated that the patients are in bed/admitted (or not in bed/discharged). Presently, Patient 2 is not in bed (discharged), and therefore physiological information is not displayed, and information indicating that the patient is not in bed (discharged) is displayed. In the same or similar manner, with respect to Patient 3 to 12, physiological information or information indicative of discharged is displayed in the patient display areas 113 to 122.

Each of the processes that are to be performed by the screen controller 230, i.e., the processes of: interchanging a display area for a specific patient with that of another patient, and displaying a resulting image on the screen; moving a display area for a specific patient, and displaying a resulting image on the screen; and inserting a display area for a specific patient, and displaying a resulting image on the screen can be performed in the same column (the first column 160 or the second column 170) or between the columns (between the first column 160 and the second column 170).

In the case where a patient display area in which information indicative of discharged is displayed is dragged and dropped onto the non-display portion 130 in accordance with instructions that are input through the inputting section 220 (see FIG. 2), the patient display area is retracted and deleted from the screen. The process of deleting a patient display area in which information indicative of discharged is displayed can be performed in all the columns (the first column 160 and the second column 170). The number of display areas that are deleted is displayed in or in the periphery of the non-display portion 130.

Since the number of deleted display areas, or that of size-reduced display areas is displayed in or in the periphery of the non-display portion 130, the number of patient display areas that are retracted into the non-display portion 130 can be easily known.

Insertion areas 131U to 140L are disposed respectively between the rows of the patient display areas in each of the columns that are arranged in 6 rows and 2 columns. The insertion areas are not disposed between the columns.

In the first column 160, the insertion area 131U is disposed in the area above the display area 111, the insertion area 131 is disposed in the border between the patient display areas 111 and 112, the insertion area 132 is disposed in the border between the patient display areas 112 and 113, the insertion area 133 is disposed in the border between the patient display areas 113 and 114, the insertion area 134 is disposed in the border between the patient display areas 114 and 115, the insertion area 135 is disposed in the border between the patient display areas 115 and 116, and the insertion area 135L is disposed in the area below the display area 116.

In the second column 170, the insertion area 136U is disposed in the area above the display area 117, the insertion area 136 is disposed in the border between the patient display areas 117 and 118, the insertion area 137 is disposed in the border between the patient display areas 118 and 119, the insertion area 138 is disposed in the border between the patient display areas 119 and 120, the insertion area 139 is disposed in the border between the patient display areas 120 and 121, the insertion area 140 is disposed in the border between the patient display areas 121 and 122, and the insertion area 140L is disposed in the area below the display area 122.

One of the patient display areas 111 to 122, or one of patient display areas that are refracted into the non-display portion 130 can be inserted into each of the insertion areas 131U to 140L.

The patient monitor 100 is configured as described above. Next, the operation of the patient monitor 100 will be described in detail with reference to FIGS. 4 to 15B.

Operation of Patient Monitor

Process of Interchanging Patient Display Areas

Figure 4:
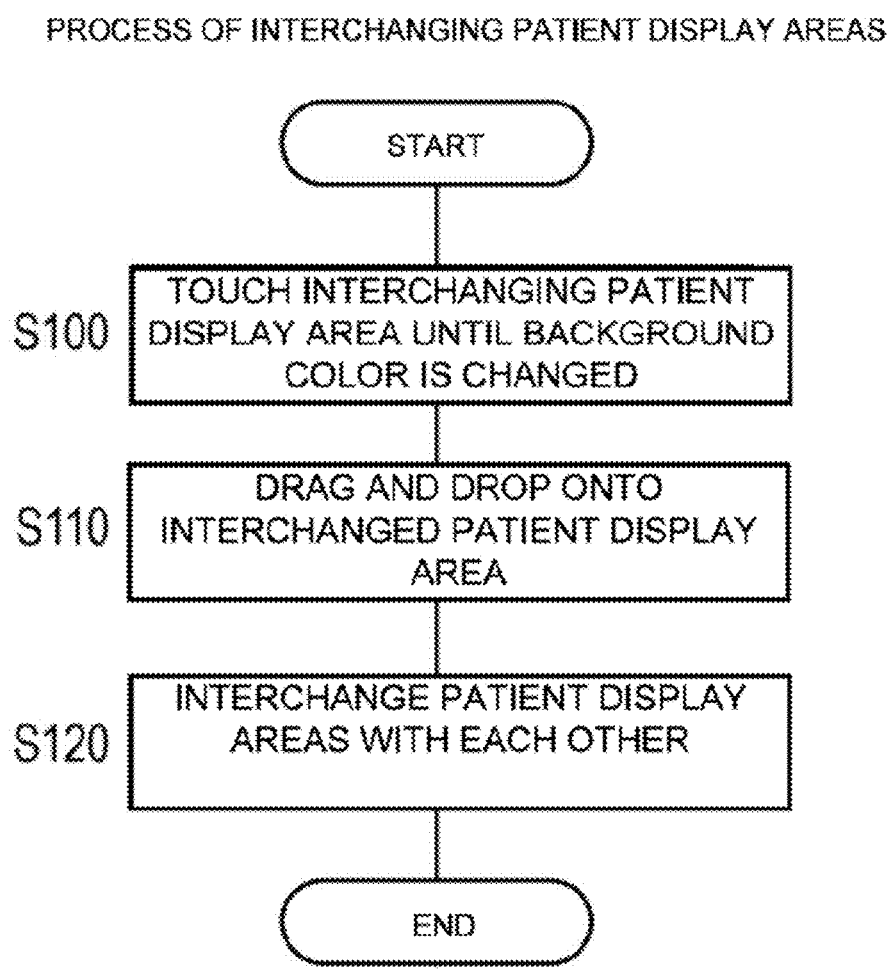
FIG. 4 is an operational flowchart of a process of interchanging patient display areas.

FIG. 4 is an operational flowchart of a process of interchanging patient display areas. The process of interchanging patient display areas can be performed in the same column (the first column 160 or the second column 170) illustrated in FIG. 3 or between the columns (between the first column 160 and the second column 170). Hereinafter, a certain patient display area that is to be interchanged with another patient display area is referred to as "interchanging patient display area," and the other patient display area that is to be interchanged with the certain patient display area is referred to as "interchanged patient display area."

As illustrated in the operational flowchart of FIG. 4, first, the operator refers a interchanging patient display area by performing a touch operation on the interchanging patient display area until the background color, which is changed at the same time with a touch operation, or after an elapse of a predetermined time period (for example, an arbitrary time period such as 3 seconds) from a touch operation, is changed (S100). The touch operation may be performed by using the finger of the operator, or a pointing device such as a mouse or a touch pad. When the touch operation is performed, the screen controller 230 (see FIG. 2) executes a program stored in the storage section 240 to prepare for the process of interchanging patient display areas.

Next, the operator drags and drops the interchanging patient display area onto the interchanged patient display area (S110). In this case, in order to enable the position of the display area of the interchange destination to be visually recognized by the operator, when a patient display area in the state where the display area is dragged is moved, and overlaps with at least a part of another display area, the background color, and the display mode of the patient ID, the outer frame, and the like of the patient display area may be changed. As a result of this operation, the screen controller 230 starts the process of interchanging patient display areas.

The screen controller 230 interchanges the interchanging patient display area with the interchanged patient display area, and causes the image that is obtained after the interchange, to be displayed on the display 110 (S120).

An example of the process of interchanging patient display areas will be specifically described. FIG. 5A illustrates a touch operation in the case where a patient display area is moved to a display area of the same column, FIG. 5B illustrates a drag-and-drop operation in the case where a patient display area is moved to a display area of the same column, and FIG. 5C illustrates a screen in a state where a patient display area is interchanged with a display area of the same column. In order to facilitate understanding of the presently disclosed subject matter, FIGS. 5A to 5C illustrate the screen of FIG. 3 in a simplified manner.

FIGS. 5A to 5C illustrate a procedure of interchanging the display area 113 for Patient 3 that is placed in the first column 160, with the display area 115 for Patient 5. In the following figures, in place of the finger, a pointer arrow is used for indicating a touch operation or a drag-and-drop operation, in older to improve the visibility.

First, the operator touches the display area 113 for Patient 3 as illustrated FIG. 5A. When the touch operation is continued for a given time period or longer, the background color of the display area 113 for Patient 3 is changed as illustrated FIG. 5B. Next, the operator performs a drag-and-drop operation by which the display area 113 for Patient 3 is moved to the position of the display area 115 for Patient 5, as illustrated in FIG. 5B. When the operator releases the display area 113 for Patient 3 at the position of the display area 115 for Patient 5, as illustrated in FIG. 5C, the display area 113 for Patient 3 is moved to the position of the display area 115 for Patient 5, and the display area 115 for Patient 5 is moved to the position of the display area 113 for Patient 3.

As a result of the above-described process, the display area 113 for Patient 3 and the display area 115 for Patient 5 can be interchanged with each other. As described above, when a display area for a specific patient is dragged end dropped onto that for another patient by the inputting section 220, the screen controller 230 causes the display areas for the specific patient and the other patient to be displayed on the screen while the display areas are interchanged with each other.

Figure 6A:
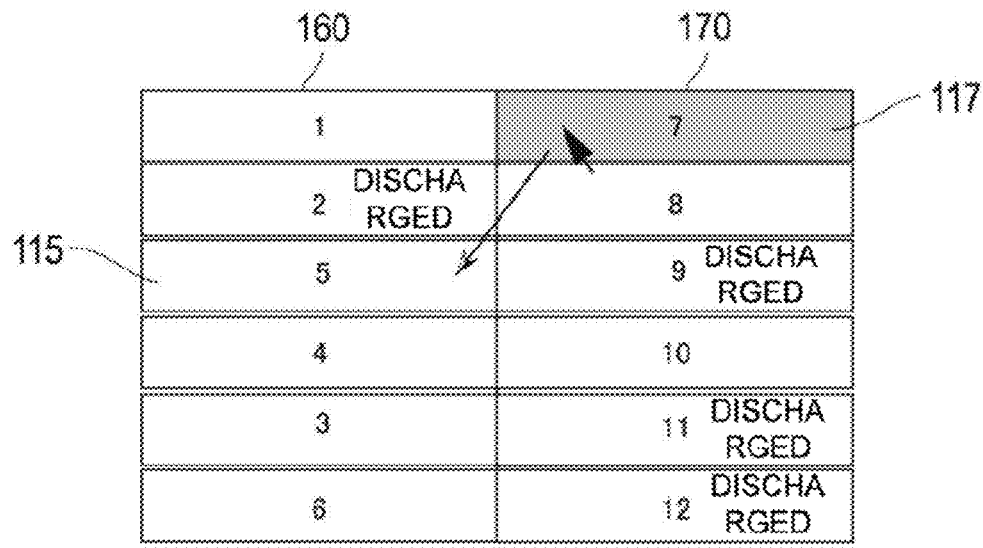
FIG. 6A illustrates a drag-and-drop operation in the case where a patient display area is moved to a display area of a different column.

Another process of interchanging patient display areas will be specifically described. FIG. 6A illustrates a drag-and-drop operation in the case where a patient display area is moved to a display area of a different column, and FIG. 6B illustrates a screen in a state where a patient display area is interchanged with a display area of a different column.

Figure 6B:
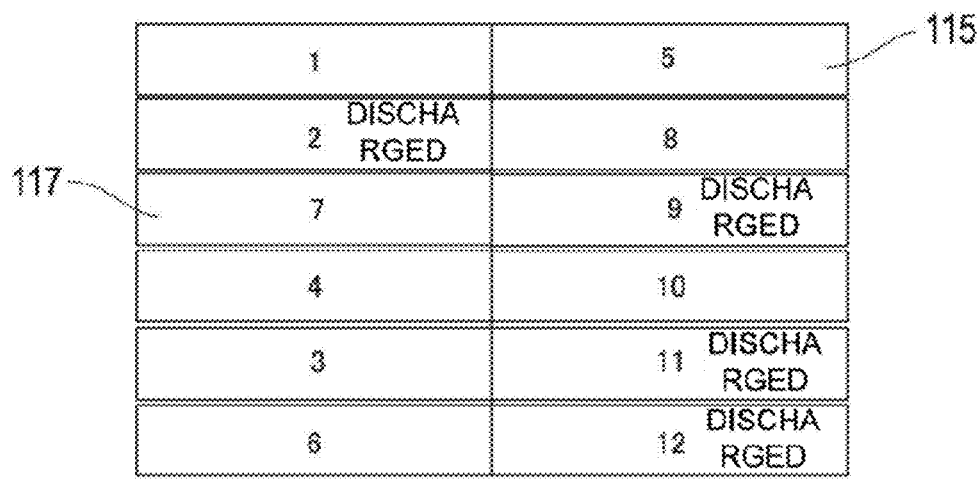
FIG. 6B illustrates a screen in a state where a patient display area is interchanged with a display area of a different column.

FIGS. 6A and 6B illustrate a procedure of interchanging the display area 117 for Patient 7 that is placed in the second column 170, with the display area 115 for Patient 5.

First, the operator touches the display area 117 for Patient 7 for a given time period or longer. When the touch operation is continued for the given time period or longer the background color of the display area 117 for Patient 7 is changed as illustrated FIG. 6A. Next, the operator performs a drag-and-drop operation by which the display area 117 for Patient 7 is moved to the position of the display area 115 for Patient 5 that is placed in the adjacent first column 160, as illustrated in FIG. 6A. When the operator releases the display area 117 for Patient 7 at the position of the display area 115 for Patient 5, as illustrated in FIG. 6B, the display area 117 for Patient 7 is moved to the position of the display area 115 for Patient 5, and the display area 115 for Patient 5 is moved to the position of the display area 117 for Patient 7.

As described above, the screen controller 230 can perform the process of interchanging a display area for a specific patient with that for another patient, and displaying a resulting image on the screen, in interchange which is performed in one column, or in that which is performed between two columns. Therefore, interchange of a display area for a specific patient with that for another patient can be freely performed in the same column or between different columns, and hence the degree of freedom of arrangement of display areas is increased.

FIG. 7 is an operational flowchart of a process of deleting a patient display area. The process of deleting a patient display area can be performed in each of the columns (the first column 160 or the second column 170) illustrated in FIG. 3.

Process of Deleting Patient Display Area

As illustrated in the operational flowchart of FIG. 7, first the operator refers a patient display area to be deleted, by performing a touch operation on the patient display area to be deleted until the background color, which is changed at the same time with a touch operation, or after an elapse of a predetermined time period (for example, an arbitrary time period such as 3 seconds) from a touch operation, is changed (S200). The touch operation may be performed by using the finger of the operator, or a pointing device such as a mouse or a touch pad. When the touch operation is performed, the screen controller 230 (see FIG. 2) executes a program stored in the storage section 240 to prepare for the process of deleting a patient display area.

Next, the operator drags and drops the patient display area to be deleted onto the non-display portion 130 (see FIG. 3) that is used for retracting a patient display area (S210). As a result of this operation, the screen controller 230 starts the process of deleting a patient display area.

Next, the screen controller 230 determines whether the patient display area that is to be deleted by the operator is a display area for patient who is not in bed (discharged), or not. If the patient display area to be deleted is not a display area for a patient who is not in bed (discharged) (S220: NO), the screen controller 230 performs no further operation, and ends the process. If the patient display area to be deleted is a display area for a patient who is not in bed (discharged) (S220: YES), by contrast, the screen controller 230 causes a message indicating that the display area for the patient is to be not displayed, to be displayed (S230).

The screen controller 230 determines whether, in response to the message, the operator gives instructions for okaying the non-display or not (S240). If the operator does not give instructions for okaying the non display (S240: NO), the screen controller 230 performs no further operation, and ends the process. If the operator gives instructions for okaying the non-display (S240: YES), the screen controller 230 retracts the patient display area that is subjected to a drag-and-drop operation, to the non-display portion 130, and deletes the patient display area from the screen (S250).

Next, the screen controller 230 causes the number of retracted patient display areas to be displayed on the lateral side of the non-display portion 130 (S260). Alternatively, the number of retracted patient display areas may be displayed overlappingly on the non-display portion 130. Then, the screen controller 230 increases the sizes of display areas for the other patients other than the deleted patient display areas (S270).

Figure 8A:
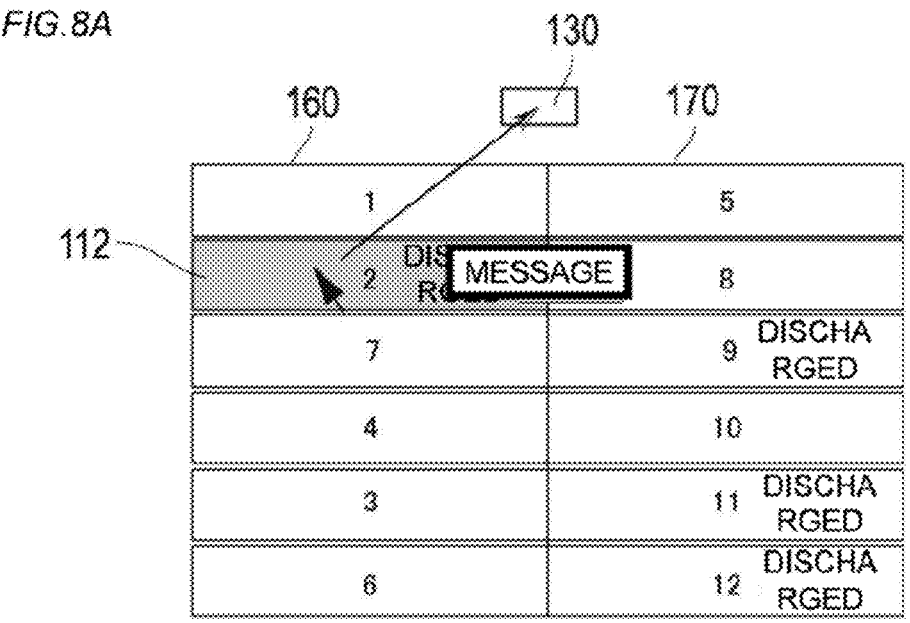
FIG. 8A illustrates a drag-and-drop operation in the case where a patient display area is moved to the non-display portion.
Figure 8B:
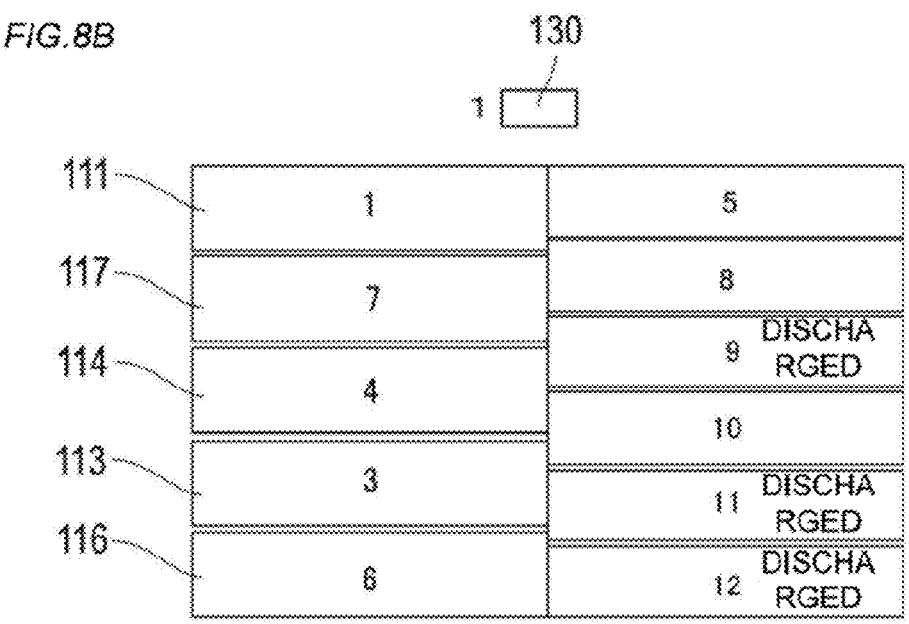
FIG. 8B illustrates a screen in a state where a patient display area is deleted.
Figure 9A:
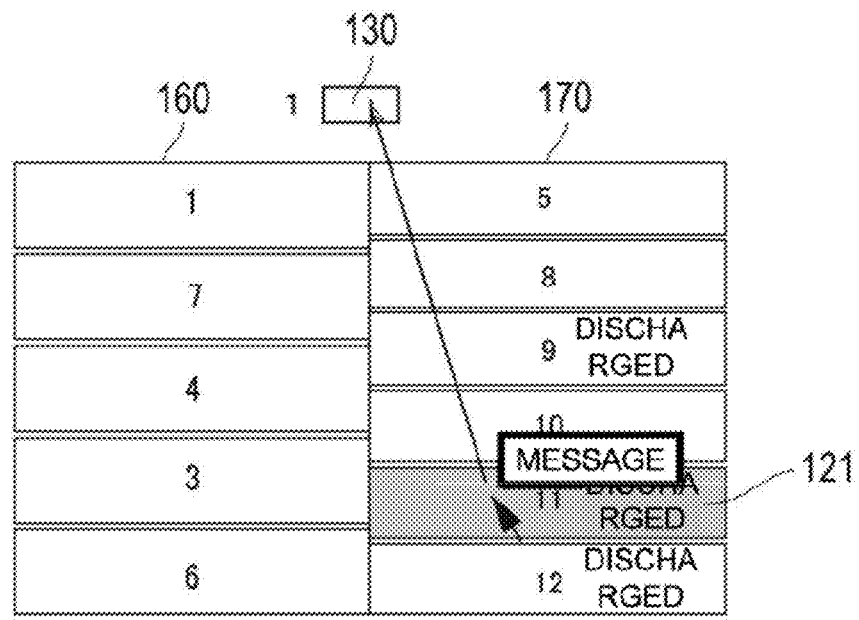
FIG. 9A illustrates a drag-and-drop operation in the case where a patient display area is moved to the non-display portion.
Figure 9B:
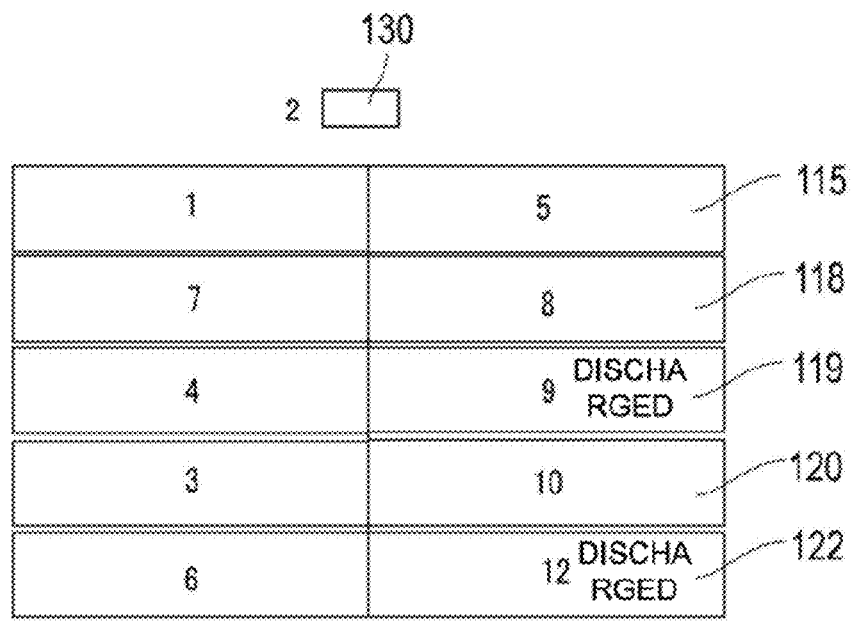
FIG. 9B illustrates a screen in a state where a patient display area is deleted.
Figure 10A:
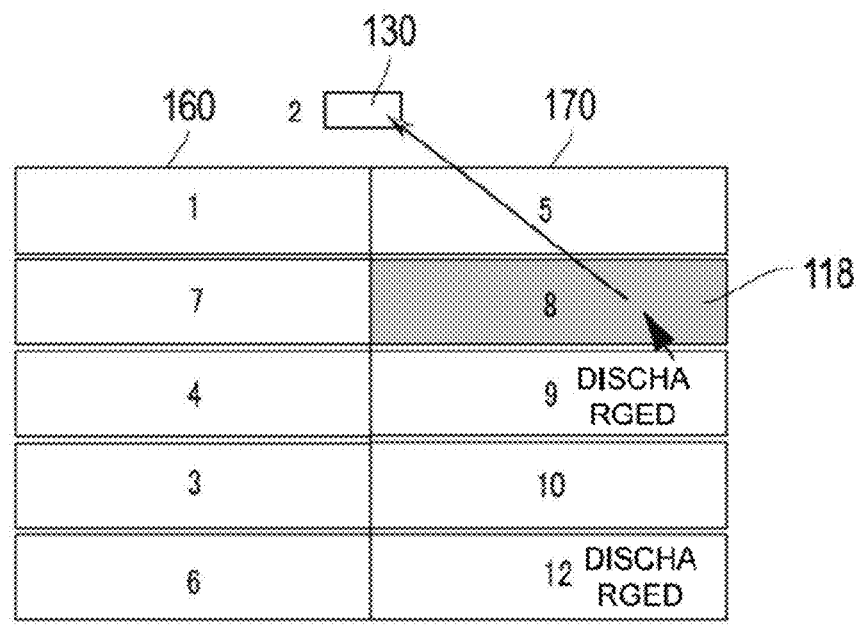
FIG. 10A illustrates a drag-and-drop operation in the case where a patient display area is moved to the non-display portion.
Figure 10B:
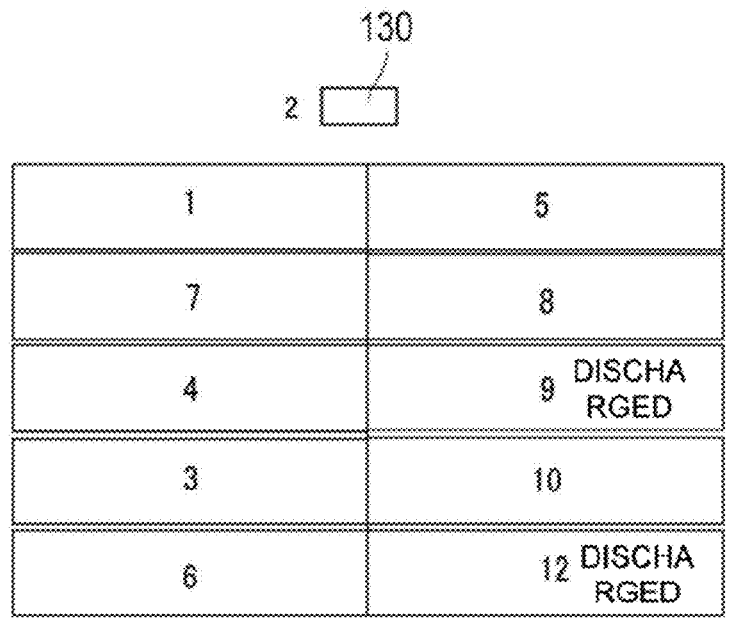
FIG. 10B illustrates a screen in a state where a patient display area is not deleted.

An example of the process of deleting a patient display area will be specifically described. FIG. 8A illustrates a drag-and-drop operation in the case where a patient display area is moved to the non-display portion, FIG. 8B illustrates a screen in a state where a patient display area is deleted. FIG. 9A illustrates a drag-and-drop operation in the case where a patient display area is moved to the non-display portion, FIG. 9B illustrates a screen in a state where a patient display area is deleted, FIG. 10A illustrates a drag-and-drop operation in the case where a patient display area is moved to the non-display portion, and FIG. 10B illustrates a screen in a state where a patient display area is not deleted.

FIGS. 8A and 8B illustrate a procedure of moving the display area 112 for Patient 2 that is placed in the first column 160, to the non-display portion 130, thereby deleting the display area from the screen.

First, the operator touches the display area 112 for Patient 2 for the given time period or longer. When the touch operation is continued for the given time period or longer, the background color of the display area 112 for Patient 2 is changed as illustrated FIG. 8A. Next, the operator performs a drag-and-drop operation by which the display area 112 for Patient 2 is moved to the position of the non-display portion 130, as illustrated in FIG. 8A. When the operator releases the display area 112 for Patient 2 at the position of the non-display portion 130, a message indicating that the display area 112 for Patient 2 is to be not displayed is displayed because the display area 112 for Patient 2 that is to be deleted is a display area for a patient who is not in bed (discharged).

When, in response to the message, the operator gives instructions for okaying the non-display, the display area 112 for Patient 2 is retracted to the non-display portion 130, and the display area 112 for Patient 2 is deleted from the first column 160 as illustrated in FIG. 8B. Then, "1" is displayed as the number of a patient display area that is retracted, on the lateral side of the non-display portion 130. Moreover, the sizes of the five display areas 111, 117, 114, 113, and 116 of other Patients 1, 7, 4, 3, and 6 other than the deleted display area 112 for Patient 2 are increased in accordance with the size (the size of the first column 160) of the screen.

As a result of the above-described process, the display area 112 for Patient 2 can be deleted from the first column 160. As described above, when a display area for a specific patient is dragged and dropped onto the non-display portion 130 by the inputting section 220, the screen controller 230 deletes the display area of the specific patient from the screen, and causes the display areas for the remaining patients to be displayed on the screen while increasing the sizes of the display areas. The screen controller 230 increases the sizes of the display areas for the remaining patients in accordance with the size of the screen.

As described above, when a display area for a patient who is not in bed (discharged) is deleted, and the sizes of display areas for remaining patients are increased, physiological information of patients can be displayed by large characters and waveforms, and therefore the physiological information can be easily viewed. When the sizes of display areas for remaining patients are increased in accordance with the size of the screen, moreover, the screen size can be effectively used.

FIGS. 9A and 9B illustrate a procedure of moving the display area 121 for Patient 11 that is placed in the second column 170, to the non-display portion 130, and then deleting it from the screen.

First, the operator touches the display area 121 for Patient 11 for a given time period or longer. When the touch operation is continued for the given time period or longer, the background color of the display area 121 for Patient 11 is changed as illustrated FIG. 9A. Next, the operator performs a drag-and-drop operation by which the display area 121 for Patient 11 is moved to the position of the non-display portion 130, as illustrated in FIG. 9A. When the operator releases the display area 121 for Patient 11 at the position of the non-display portion 130, a message indicating that the display area 121 for Patient 11 is to be not displayed is displayed because the display area 121 for Patient 11 that is to be deleted is a display area for a patient who is not in bed (discharged).

When, in response to the message, the operator gives instructions for okaying the non-display, the display area 121 for Patient 11 is retracted to the non-display portion 130, and the display area 121 for Patient 11 is deleted from the second column 170 as illustrated in FIG. 9B. Then, "2" is displayed as the number of patient display areas that are retracted, on the lateral side of the non-display portion 130. The sizes of the five display areas 115, 118, 119, 120, and 122 of other Patients 5, 8, 9, 10, and 12 other than the deleted display area 121 for Patient 11 are increased in accordance with the size (the size of the second column 170) of the screen.

As a result of the above-described process, the display area 121 for Patient 11 can be deleted front the second column 170. As described above, the screen controller 230 can execute the process of deleting a display area for a specific patient from the screen, for each of the columns. Since the process of increasing the sizes of display areas for patients can be performed for each of the columns, physiological information of patients can be displayed by large characters and waveforms for each column, and therefore the physiological information can be easily viewed. When the sizes of display areas for remaining patients are increased in accordance with the size of the screen, moreover, the screen size can be effectively used.

FIGS. 10A and 10B illustrate a procedure of moving the display area 118 for Patient 8 that is placed in the second column 170, to the non-display portion 130, and deleting it from the screen.

First, the operator touches the display area 118 for Patient 8 for a given time period or longer. When the touch operation is continued for the given time period or longer, the background color of the display area 118 for Patient 8 is changed as illustrated FIG. 10A. Next, the operator performs a drag-and-drop operation by which the display area 118 for Patient 8 is moved to the position of the non-display portion 130, as illustrated in FIG. 10A. When the operator releases the display area 118 for Patient 8 at the position of the non-display portion 130, the screen controller 230 ends the process without deleting the display area 118 for Patient 8, and performing a further operation because the display area 118 for Patient 8 that is to be deleted is not a display area for a patient who is not in bed (discharged). As illustrated in FIG. 10B, therefore, a screen that is strictly identical with FIG. 10A is displayed.

As described above, only a display area for a patient who is not in bed (discharged) is retracted to the non-display portion 130, and therefore it is possible to prevent a patient display area where physiological information is displayed, from being deleted.

FIG. 11 is on operational flowchart of a process of moving a patient display area. A process of moving a patient display area can be performed in the same column (the first column 160 or the second column 170) illustrated in FIG. 3, or between the columns (between the first column 160 and the second column 170).

Process of Moving Patient Display Area

As illustrated in the operational flowchart of FIG. 11, first, the operator refers a patient display area to be moved, by performing a touch operation on the patient display area until the background color, which is changed at the same time with a touch operation, or after an elapse of a predetermined time period (for example, an arbitrary time period such as 3 seconds) from a touch operation, is changed (S300). The touch operation may be performed by using the finger of the operator, or a pointing device such as a mouse or a touch pad. When the touch operation is performed, the screen controller 230 (see FIG. 2) executes a program stored in the storage section 240 to prepare for the process of moving a patient display area.

Next, the operator drags end drops the patient display area to be moved, onto an insertion area that is the movement destination, and that is in the border between adjacent display areas for other two patients (S310). In this case, in order to enable the position of the display area that is the movement destination, and that is in the border between adjacent display areas for other two patterns, to be visually recognized by the operator, in the case where the display area in the state where the display area is dragged is moved, the display mode of the insertion area may be changed when at least a part of the display area overlaps with the insertion area into which insertion is enabled. As a result of this operation, the screen controller 230 starts the process of moving a patient display area.

The screen controller 230 inserts the patient display area to be moved, into the insertion area of the movement destination (S320). Next, the screen controller 230 adjusts the sizes of the display areas of the all columns, i.e., the columns on the side into which the patient display area is inserted, and those on the side from which the patient display area is deleted, and causes the screen in which the sizes have been adjusted, to be displayed on the display 110 (S330).

As described above, when a display area for a specific patient is dragged and dropped by the inputting section 220 onto an insertion area that is in the border between adjacent display areas for other two patients, or the vicinity of the insertion area that is in the border between adjacent display areas for other two patients, the screen controller 230 executes the process of inserting the display area for the specific patient into the insertion area, and displaying a resulting image on the screen.

When a display area for a specific patient is made insertable into an insertion area, a patient display area can be easily moved. When the display areas of the all columns are made adjustable, the screen size can be effectively used.

Figure 12A:
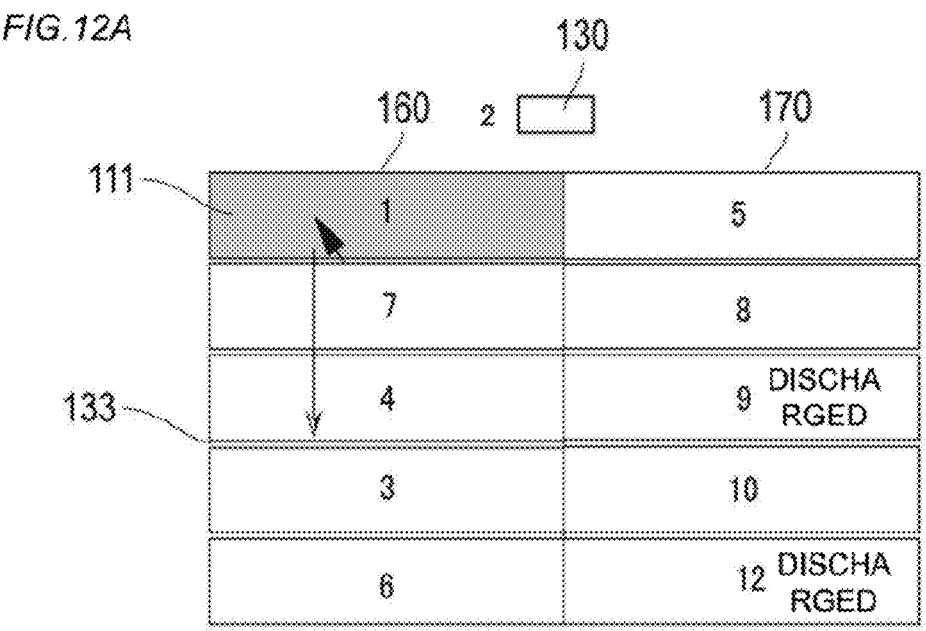
FIG. 12A illustrates a drag-and-drop operation in the case where a patient display area is moved to an insertion area of the same column.

An example of the process of moving a patient display area will be specifically described. FIG. 12A illustrates a drag-and-drop operation in the case where a patient display area is moved to an insertion area of the same column, FIG. 12B illustrates a screen in a state where a patient display area is moved in the same column, FIG. 13A illustrates a drag-and-drop operation in the case where a patient display area is moved to an insertion area of a different column, and FIG. 13B illustrates a screen in a state where a patient display area is moved to a different column.

Figure 12B:
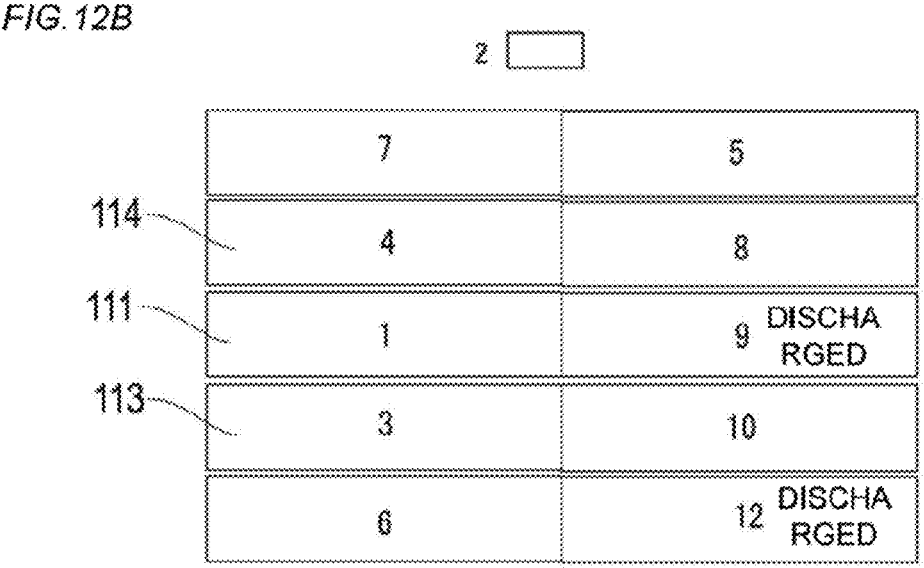
FIG. 12B illustrates a screen in a state where a patient display area is moved in the same column.
Figure 13A:
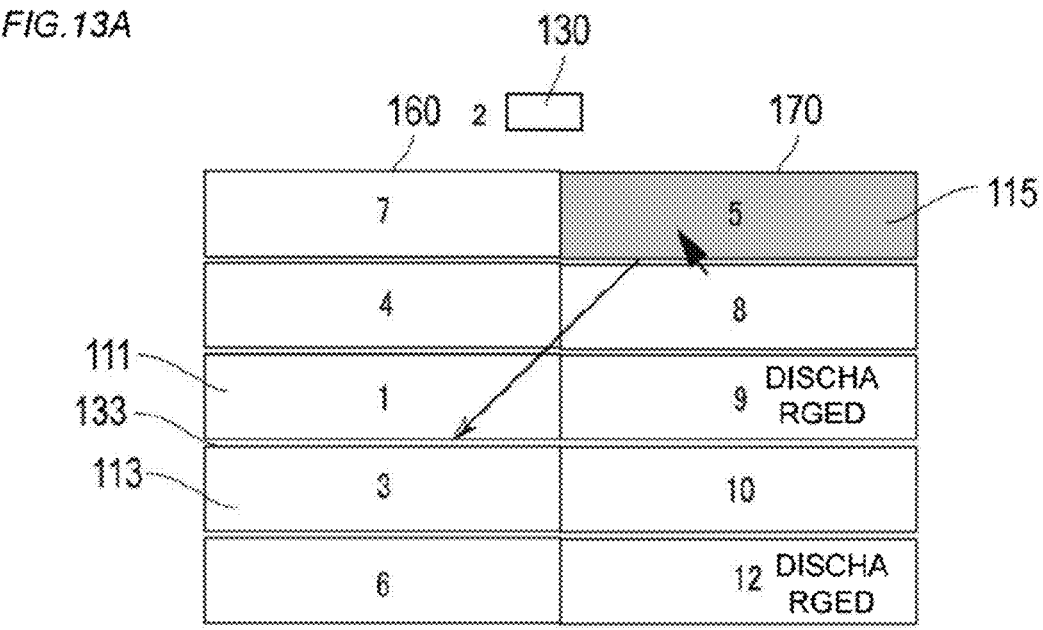
FIG. 13A illustrates a drag-and-drop operation in the case where a patient display area is moved to an insertion area of a different column.
Figure 13B:
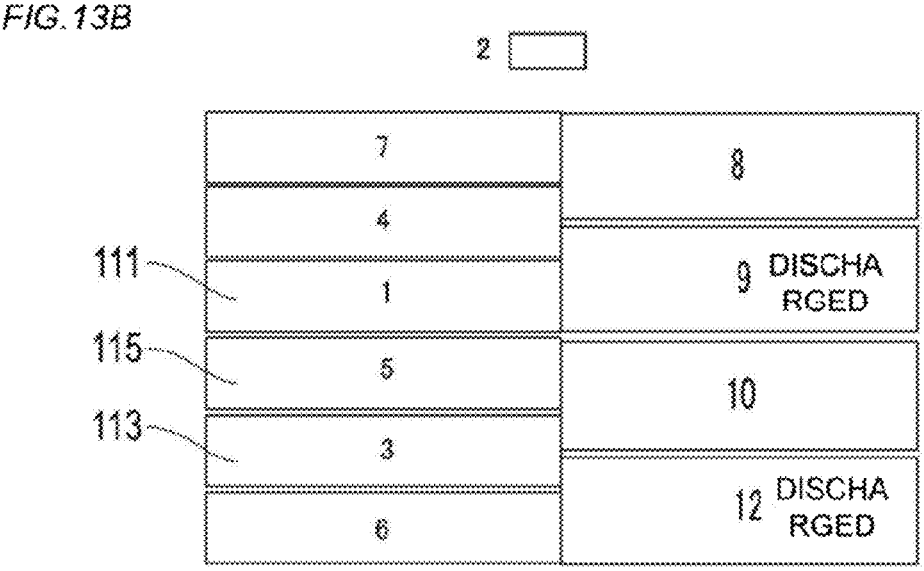
FIG. 13B illustrates a screen in a state where a patient display area is moved to a different column.

FIGS. 12A and 12B illustrate a procedure of moving the display area 111 for Patient 1 that is placed in the first column 160, to the insertion area 133 to move the display area 111 for Patient 1 between the display area 114 for Patient 4 and the display area 113 for Patient 3.

First, the operator touches the display area 111 for Patient 1 for a given time period or longer. When the touch operation is continued for the given time period or longer, the background color of the display area 111 for Patient 1 is changed as illustrated FIG. 12A. Next, the operator performs a drag-and-drop operation by which the display area 111 for Patient 1 is moved to the position of the insertion area 133, as illustrated in FIG. 12A. When the operator releases the display area 111 for Patient 1 at the position of the insertion area 133, the display area 111 for Patient 1 is moved between the display area 114 for Patient 4 and the display area 113 for Patient 3 as illustrated in FIG. 12B.

At this time, the screen controller 230 executes a process of adjusting the sizes of the all patient display areas that are placed in the first column 160 and the second column 170, and displaying a resulting image on the screen. In this case, the arrangement of display areas in the same column is simply changed, and therefore the number of display areas arranged in the same column is unchanged. Even in the image after the adjustment, therefore, the sizes of the display areas are identical with those before the movement as illustrated in FIG. 12B.

The screen controller 230 can execute the process of moving a display area for a specific patient, and displaying a resulting image on the screen, on one column. In the case where a plurality of display areas are arranged in plural rows and plural columns on the screen of the display 110, patient display areas of each of the columns can be moved.

FIGS. 13A and 13B illustrate a procedure of moving the display area 115 for Patient 5 that is placed in the second column 170, to the insertion area 133 in the adjacent first column 160 to move the display area 115 for Patient 5 between the display area 111 for Patient 1 and the display area 113 for Patient 3.

First, the operator touches the display area 115 for Patient 5 for a given time period or longer. When the touch operation is continued for the given time period or longer, the background color of the display area 115 for Patient 5 is changed as illustrated FIG. 13A. Next, the operator performs a drag-and-drop operation by which the display area 115 for Patient 5 is moved to the position of the insertion area 133 of the adjacent column, as illustrated in FIG. 13A. When the operator releases the display area 115 for Patient 5 at the position of the insertion area 133, the display area 115 for Patient 5 is moved between the display area 111 for Patient 1 and the display area 113 for Patient 3 as illustrated in FIG. 13B.

At this time, the screen controller 230 executes a process of adjusting the sizes of the all patient display areas that are placed in the first column 160 and the second column 170, and displaying a resulting image on the screen. In this case, as illustrated in FIG. 13B, the sizes of the patient display areas that are placed in the first column 160 are reduced, and those of the patient display areas that are placed in the second column 170 are increased.

In the case where a process of moving a display area for a specific patient, and displaying a resulting image on the screen is to be performed between two columns, as described above, the screen controller 230 executes the process of reducing the sizes of all patient display areas in the column that is the movement destination of the display area for the specific patient, increasing those of all patient display areas in the column that is the movement source, and displaying a resulting image on the screen.

In the case where a plurality of display areas are arranged in plural rows and plural columns on the screen of the display 110, the sizes of patient display areas of each of the columns can be increased or reduced, and therefore the screen size can be effectively used.

Figure 14:
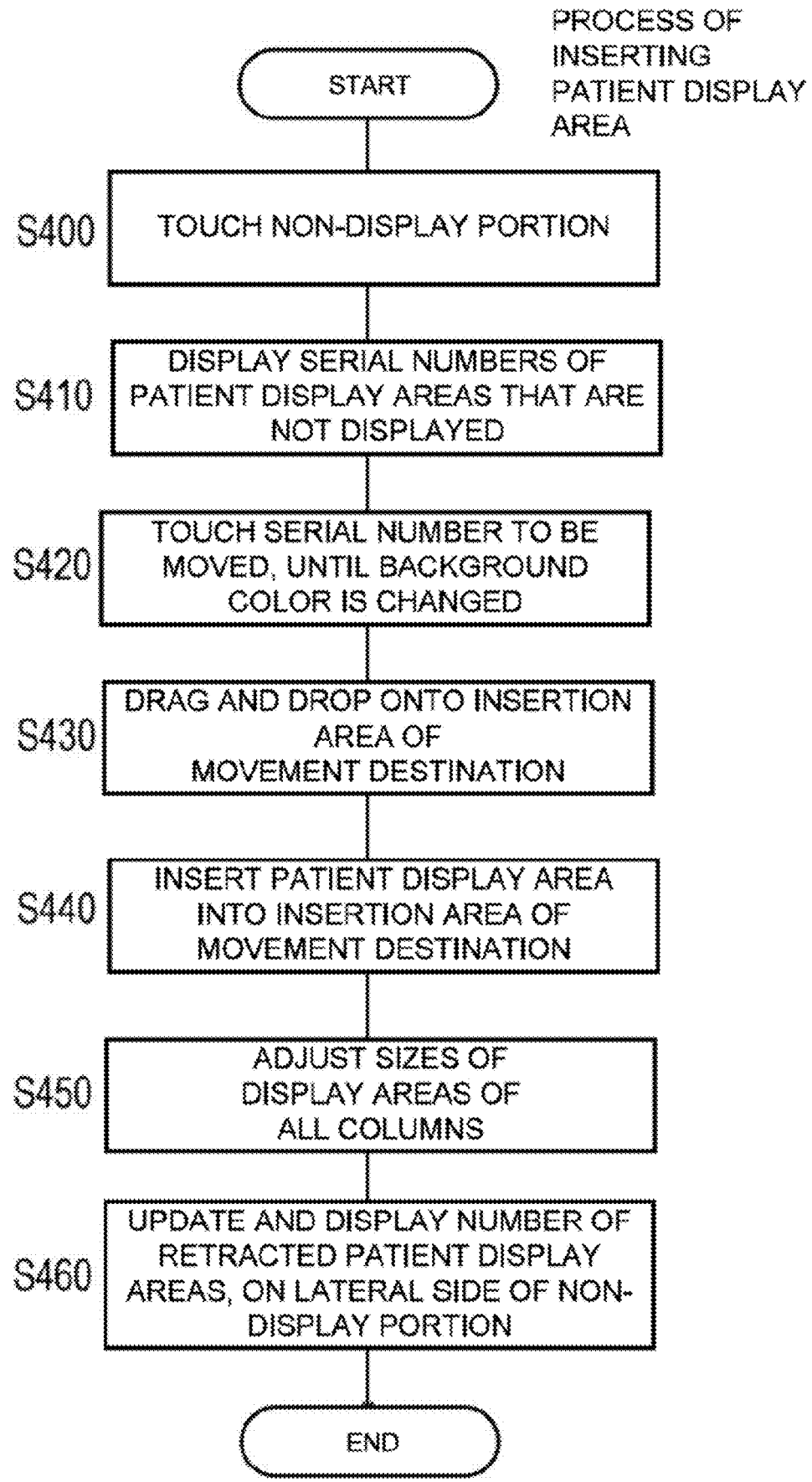
FIG. 14 is an operational flowchart of a process of inserting a patient display area.

FIG. 14 is an operational flowchart of a process of inserting a patient display area. The process of insetting a patient display area can be performed in each of the columns (the first column 160 or the second column 170) illustrated in FIG. 3.

Process of Inserting Patient Display Area

As illustrated in the operational flowchart of FIG. 14, first, the operator touches the non-display portion 130 (see FIG. 3) (S400). The screen controller 230 causes the serial numbers of patient display areas that are set so as not to be displayed, to be displayed in a pop-up window that is on the lateral side of the non-display portion 130 (S410). Next, the operator continues to touch the serial number of the display area to be moved, until the background color is changed (for example, for 3 seconds) (S420). The touch operation may be performed by using the finger of the operator, or a pointing device such us a mouse or a touch pad. When the touch operation of S420 is performed, the screen controller 230 (see FIG. 2) executes a program stored in the storage section 240 to prepare for the process of inserting a patient display area.

Next, the operator drags and drops the serial number of the display area to be moved, onto the insertion area of the movement destination that is in the border between adjacent display areas for two patients (S430). As a result of this operation, the screen controller 230 starts the process of inserting a patient display area.

The screen controller 230 causes the patient display area that corresponds to the moved serial number, to be inserted into the insertion area of the movement destination (S440). Next, the screen controller 230 adjusts the sizes of the display areas of the all columns, and causes the adjusted image to be displayed on the display 110 (S450). Then, the screen controller 230 updates the number of retracted patient display areas, and causes the updated number to be displayed on the lateral side of the non-display portion (S460).

As described above, the screen controller 230 can execute the process of inserting a display area for a specific patient from the non-display portion 130 into the insertion area, and displaying a resulting image on the screen. In the case where a plurality of display areas are arranged in plural rows and plural columns on the screen of the display 110, a display area for a specific patient of each of the columns can be inserted lump from the non-display portion 130 into the insertion area.

Figure 15A:
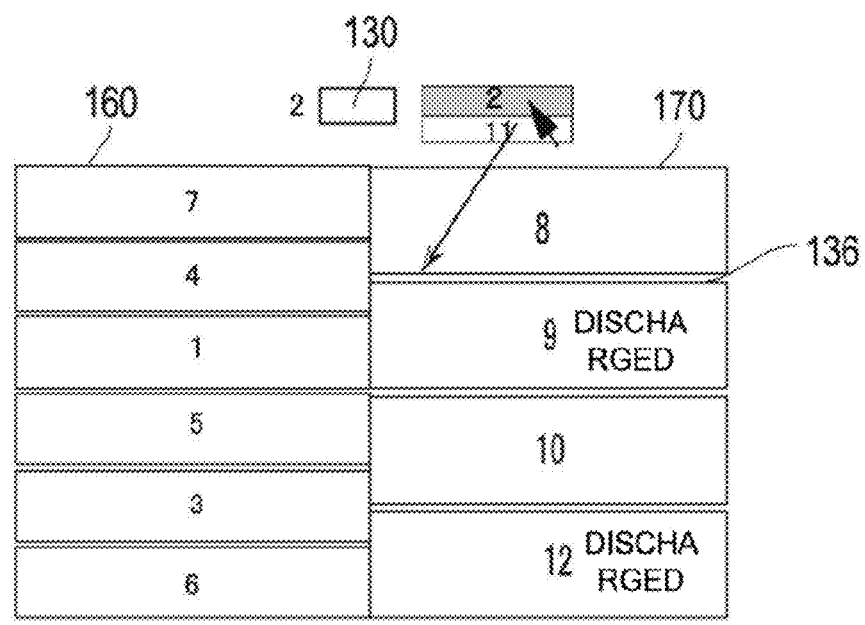
FIG. 15A illustrates a drag-and-drop operation in the case where a patient display area is moved from the non-display portion to an insertion area.
Figure 15B:
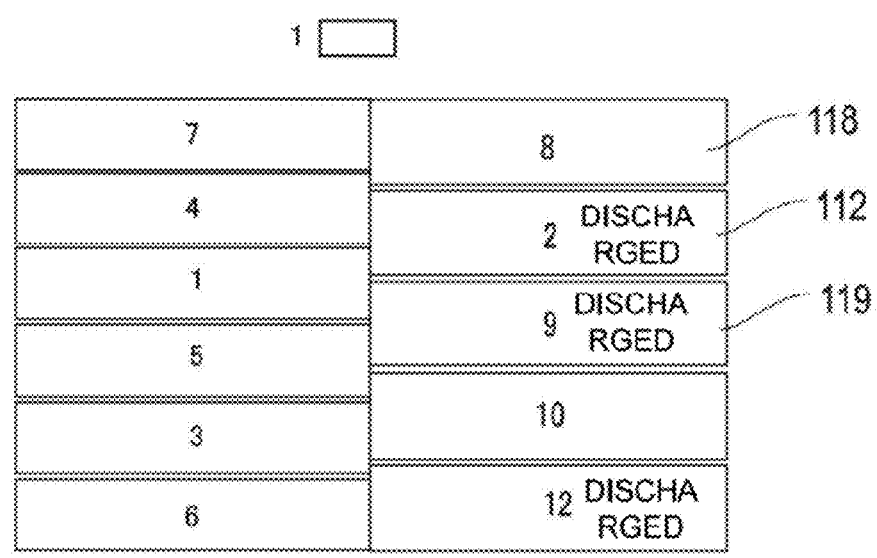
FIG. 15B illustrates a screen in a state where a patient display area is inserted into an insertion area.

FIG. 15A illustrates a drag-and-drop operation in the case where a patient display area is moved from the non-display portion to an insertion area, and FIG. 15B illustrates a screen in a state where a patient display area is inserted into an insertion area.

First, the operator taps the non-display portion 130. This tapping operation causes a pop-up window such as illustrated in FIG. 15A to be displayed on the lateral side of the non-display portion 130, and the serial numbers (in this example, 2 and 11) of patient display areas that are set so as not to be displayed, to be displayed in the pop-up window. Then, the operator touches the serial number (in this example, 2) that is among the serial numbers displayed in the pop-up window, and that corresponds to the display area to be moved, for a given time period or longer. When the touch operation is continued for the given time period or longer, as illustrated in FIG. 15A, the background color of the area where the serial number "2" is displayed is changed.

As illustrated in FIG. 15A, next, the operator performs a drag-and-drop operation by which the serial number "2" is moved to the position of the insertion area 136 in the second column 170. When the operator releases the serial number "2" at the position of the insertion area 136 as illustrated in FIG. 15B, the display area 112 for Patient 2 corresponding to the serial number "2" is inserted between the display area 118 for Patient 8 and the display area 119 for Patient 9.

At this time, the screen controller 230 executes a process of adjusting the sizes of the all patient display areas that are placed in the first column 160 and the second column 170, and displaying a resulting image on the screen. In this case, as illustrated in FIG. 15B, the sizes of the patient display areas that are placed in the first column 160 remain unchanged, and those of the patient display areas that are placed in the second column 170 are reduced.

Next, the screen controller 230 updates the number of the retracted patient display areas that is displayed on the lateral side of the non-display portion 130, from 2 to 1, and causes the resulting image to be displayed as illustrated in FIGS. 15A and 15B.

In the case where a plurality of display areas are arranged in plural rows and plural columns on the screen of the display 110, the sizes of patient display areas in the column into which a patient display area is inserted can be reduced, and therefore the screen size can be effectively used.

According to the patient monitor 100 of the embodiment, as described above, patient display areas can be freely interchanged, deleted, moved, or inserted within the screen by a simple operation.

The embodiment of the patient monitor 100 of the presently disclosed subject matter has been described above. The above-described embodiment does not limit the technical scope of the presently disclosed subject matter. For example, the patient monitor may be configured so that, in the case where a patient display area is to be moved, the operator can select the display area by simply touching the display area for the predetermined time period even when the background color is not changed. The patient monitor may be configured so that, in the case where a display area is to be selected, the selection of the display area can be performed by, when the operator touches the display area, notifying of the selection in a display mode such as generation of a sound indicating that the selection is completed, or the like. A plurality of display areas may be selected through the inputting section, and movement of display areas to the non-display portion, interchange of the positions of the display areas with those of other display areas, or insertion of the display areas between other display areas may be performed. A plurality of display areas that are moved to the non-display portion may be selected, and then moved to a screen for display areas for patients who are in bed (admit). With respect to the number of deleted display areas, the non-display portion 130 may be provided with another display mode in which, in addition to the number of deleted display areas, information simply indicating existence or non-existence of deleted display areas is displayed. It is a matter of course that the patient monitor 100 of the presently disclosed subject matter includes all specific examples that can be modified by those skilled in the art.

What is claimed is:

1. A patient monitor comprising:
an acquiring section computer configured to acquire physiological information of a plurality of patients;
a display configured to display the physiological information of the plurality of patients that is acquired by the acquiring section computer, on a screen;
a screen controller configured to set a plurality of display areas in the screen of the display, and, in each of the plurality of display areas, control how the physiological information of a patient that is acquired by the acquiring section computer is displayed; and
a user interface configured to input instructions for moving the display area for each of the patients,
wherein in accordance with instructions input through the user interface, the screen controller is configured to execute one of processes of: interchanging a display area for a specific patient with a display area for another patient, and displaying a resulting image on the screen; deleting the display area for the specific patient from the screen; moving the display area for the specific patient, and displaying a resulting image on the screen; and inserting the display area for the specific patient, and displaying a resulting image on the screen;
wherein each of the plurality of display areas (i) is associated with a bed and/or room of a corresponding patient of the plurality of patients and (ii) contains information by which admit/discharge of the corresponding patient is distinguishable.

2. The patient monitor according to claim 1,
wherein when the display area for the specific patient is moved to a display area for another patient by the user interface, the screen controller executes a process of interchanging the display area for the specific patient with the display area for the other patient, and displaying a resulting image on the screen.

3. The patient monitor according to claim 1,
wherein when the display area for the specific patient is moved to a non-display portion that is disposed in the screen, by the user interface, the screen controller deletes the display area for the specific patient from the screen.

4. The patient monitor according to claim 3,
wherein the screen controller executes a process of deleting the display area for the specific patient from the screen, increasing sizes of display areas for remaining patients, and causing the display areas to be displayed on the screen.

5. The patient monitor according to claim 3,
wherein the screen controller causes information of a deleted display area to be displayed in a distinguishable manner in or in a periphery of the non-display portion.

6. The patient monitor according to claim 1,
wherein when the display area for the specific patient is moved by the user interface to an insertion area that is in a border between adjacent display areas for other two patients, or to a vicinity of an insertion area that is in a border between adjacent display areas for other two patients, the screen controller executes a process of inserting the display area for the specific patient into the insertion area, and displaying a resulting image on the screen.

7. The patient monitor according to claim 1,
wherein when the display area for the specific patient is moved by the user interface from a non-display portion that is disposed in the screen, to an insertion area that is in a border between adjacent display areas for other two patients, or to a vicinity of an insertion area that is in a border between adjacent display areas for other two patients, the screen controller executes a process of inserting the display area for the specific patient into the insertion area, reducing sizes of all display areas for patients, and displaying a resulting image on the screen.

8. The patient monitor according to claim 1,
wherein the screen controller is configured to cause a plurality of display areas to be displayed on the screen of the display while being arranged in plural rows and plural columns, and executes a process of interchanging the display area for the specific patient with a display area for another patient, and displaying a resulting image on the screen, in an operation of interchanging the display areas in one column or an operation of interchanging the display areas between two columns.

9. The patient monitor according to claim 1,
wherein the screen controller is configured to cause a plurality of display areas to be displayed on the screen of the display while being arranged in plural rows and plural columns, and executes a process of deleting the display area for the specific patient from the screen, in each of the columns.

10. The patient monitor according to claim 1,
wherein the screen controller is configured to cause a plurality of display areas to be displayed on the screen of the display while being arranged in plural rows and plural columns, and executes a process of inserting the display area for the specific patient into an insertion area, and displaying a resulting image on the screen, in each of the columns.

11. The patient monitor according to claim 1,
wherein the screen controller is configured to cause a plurality of display areas to be displayed on the screen of the displaying section while being arranged in plural rows and plural columns, and, in a case where a process of moving the display area for the specific patient, and displaying a resulting image on the screen is to be performed between two columns, executes a process of reducing sizes of all display areas for patients in a column that is a movement destination of the display area for the specific patient, increasing sizes of all display areas for patients in a column that is a movement source, and displaying a resulting image on the screen.

12. The patient monitor according to claim 1,
wherein the screen controller is configured to cause a plurality of display areas to be displayed on the screen of the display while being arranged in plural rows and plural columns, and executes a process of inserting the display area for the specific patient into an insertion area, reducing sizes of all display areas for patients, and displaying a resulting image on the screen.

13. The patient monitor according to claim 1,
wherein the user interface is a pointing device which includes a mouse, a touch pad, or a touch panel, and through which instructions for moving display areas for patients can be given by a drag-and-drop operation.

14. The patient monitor according to claim 1,
wherein the display area for each of the patients is information by which the patient can be identified.

15. The patient monitor according to claim 1,
wherein the screen controller being configured to delete the display area for the specific patient from the screen is based on a determination by the screen controller.

16. The patient monitor according to claim 1,
wherein the at least one processor and memory being configured to delete the display area for the specific patient from the screen is based on a determination by the at least one processor and memory.

17. A patient monitor comprising:
at least one processor and memory configured to:
  acquire physiological information of a plurality of patients;
  display the physiological information on a screen;
  set a plurality of display areas in the screen, and that, in each of the set display areas, controls a display of the physiological information of a patient that is acquired;
user interface configured to input instructions for moving the display area for each of the patients, and
wherein in accordance with instructions input by the user interface, the at least one processor and memory is configured to execute one of processes of:
interchanging a display area for a specific patient with a display area for another patient, and displaying a resulting image on the screen;
deleting the display area for the specific patient from the screen;
moving the display area for the specific patient, and displaying a resulting image on the screen; and
inserting the display area for the specific patient, and displaying a resulting image on the screen;
wherein each of the plurality of display areas (i) is associated with a bed and/or room of a corresponding patient of the plurality of patients and (ii) contains information by which admit/discharge of the corresponding patient is distinguishable.

18. The patient monitor according to claim 17, wherein the display area for each of the patients is information by which the patient can be identified.

* * * * *